US011633624B2

(12) United States Patent
Heese et al.

(10) Patent No.: US 11,633,624 B2
(45) Date of Patent: Apr. 25, 2023

(54) RESOURCE SCHEDULING IN ADAPTIVE RADIATION THERAPY PLANNING

(71) Applicant: KONINKLIJKE PHILIPS N.V., Eindhoven (NL)

(72) Inventors: Harald Sepp Heese, Hamburg (DE); Torbjoern Vik, Hamburg (DE); Steffen Renisch, Hamburg (DE); Daniel Bystrov, Hamburg (DE); Heinrich Schulz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/558,509

(22) Filed: Sep. 3, 2019

(65) Prior Publication Data

US 2020/0069969 A1  Mar. 5, 2020

(30) Foreign Application Priority Data

Sep. 4, 2018 (EP) .................................. 18192414

(51) Int. Cl.
*G16H 20/40* (2018.01)
*A61N 5/10* (2006.01)
*G16H 40/20* (2018.01)

(52) U.S. Cl.
CPC .......... *A61N 5/1038* (2013.01); *G16H 20/40* (2018.01); *G16H 40/20* (2018.01); *A61N 2005/1041* (2013.01)

(58) Field of Classification Search
CPC ......... A61N 5/1038; A61N 2005/1041; G16H 40/20; G16H 20/40; G16H 50/70;
(Continued)

(56) References Cited

U.S. PATENT DOCUMENTS 9,764,162 B1 * 9/2017 Willcut ................. G06T 7/0014
10,675,483 B2 * 6/2020 Vik ........................ G16H 50/30
(Continued)

FOREIGN PATENT DOCUMENTS

CN     107888669 A   4/2018
JP    2000222507 A   8/2000
(Continued)

OTHER PUBLICATIONS

Brown, Elizabeth et al "Head and Neck Adaptive Radiotherapy: Predicting the Time to Replan" Asia-Pacific Journal of Clinical Oncology, Jul. 2016.
(Continued)

*Primary Examiner* — Jason S Tiedeman
*Assistant Examiner* — Liza Tony Kanaan

(57) ABSTRACT

A resource management system for better operation of a plurality of devices. The system comprises an input interface (IN) for receiving input data including one or more characteristics of at least one work object (P1-P3) and/or including context data. The at least one work object (P1-P3) can be processed by one or more processing devices ($M_{ij}$). The said processing is specified in a respective work specification (S1-S3). A predictor component (PC) of the system is configured to predict, based on the input data, a change to the work specification. The system comprises an output interface (OUT) for providing output data that represents said predicted change.

22 Claims, 5 Drawing Sheets

(58) Field of Classification Search
CPC ...... G06N 5/003; G06N 20/10; G06N 3/0454; G06N 3/08; G06N 3/0445
See application file for complete search history.

(56) References Cited

U.S. PATENT DOCUMENTS

| | | | |
|---|---|---|---|
| 2006/0265136 A1* | 11/2006 | Kouchi | G16H 50/20 |
| | | | 702/19 |
| 2010/0303205 A1 | 12/2010 | Kapoor | |
| 2011/0282684 A1 | 11/2011 | Chua | |
| 2013/0204067 A1* | 8/2013 | Nord | A61N 5/1038 |
| | | | 600/1 |
| 2016/0144198 A1 | 5/2016 | Lof | |
| 2016/0300024 A1* | 10/2016 | Janssen | G06Q 10/06 |
| 2018/0166172 A1* | 6/2018 | Fidone | G16H 50/30 |
| 2018/0247715 A1* | 8/2018 | Kumar | G16H 15/00 |

FOREIGN PATENT DOCUMENTS

| | | |
|---|---|---|
| JP | 2008217325 A | 9/2008 |
| WO | 200077665 A2 | 12/2000 |
| WO | 2011110958 A1 | 9/2011 |
| WO | 2015082253 A1 | 6/2015 |
| WO | 2016145251 A1 | 9/2016 |
| WO | 2017089097 A1 | 6/2017 |
| WO | 2017120646 A1 | 7/2017 |

OTHER PUBLICATIONS

Huqqani, Altaf Ahmad et al "Multicore and GPU Parallelization of Neural Networks for Face Recognition", International Conference on Computation Science, SciVerse Sciencedirect, 2013.

Pfugfelder et al "A Comparison of Three Optimization Algorithms for Intensity Modulated Radiation Therapy", Z Med Phys. vol. 18, No. 2, 2008, pp. 111-119 (Abstract Only).

* cited by examiner

RESOURCE SCHEDULING IN ADAPTIVE RADIATION THERAPY PLANNING

FIELD OF THE INVENTION

The invention relates to system of resource management, to a method of resource management, to a computer program element, and to a computer readable medium.

BACKGROUND OF THE INVENTION

Radiation therapy (RT) treatment plan adaptation in case of unexpected tumor response is one of the most common forms of adaptive RT.

Plan adaptation involves a number of different pieces of equipment, such as a CT scanner, image analysis tools, medical record database, and a treatment planning system.

To date however it is unknown when a need for RT plan adaption will arise and medical facilities are left to act ad-hoc when the need so arises which makes planning and the efficient use of the above mentioned resources difficult.

Similar considerations arise in other parts of industry such as production, assembly etc., where a complex series of inter-dependent tasks need to be scheduled.

SUMMARY OF THE INVENTION

There may therefore be a need for system and method to better manage resources, or to better control operation of the said resources.

The object of the present invention is solved by the subject matter of the independent claims where further embodiments are incorporated in the dependent claims. It should be noted that the following described aspect of the invention equally applies to the method of resource management, to the computer program element and to the computer readable medium.

According to a first aspect of the invention there is provided a resource management system, comprising:

an input interface for receiving input data including one or more characteristics of at least one work object and/or including context data, the at least one work object to be processed by one or more processing devices, the said processing being specified in a respective work specification; and a predictor component configured to predict, based on the input data, a change to the work specification; and output interface for providing output data that represents said predicted change.

In embodiments, the specification specifies a period of time for the said processing.

In embodiments, the said output data comprises a probability density or distribution over said period, said period comprising at least one time or interval, the probability density or distribution indicative of a probability of the predicted change to occur at a given one of the at least one time intervals.

In embodiments, there is plurality of work objects, wherein the system comprises an accumulator configured to accumulate the output data for the plurality of work objects.

In embodiments, the output data includes an indication of the expected workload, due to the predicted change, for at least one of the devices or for at least one category of devices.

In embodiments the system comprises a visualizer configured to effect a visualization of the said output data or of the accumulated output data on at least one display device.

The accumulator allows analyzing a situation where more than one work object is to be processed in a certain processing time period. The visualizer can be configured to display accumulated or averaged probabilities of expected changes to the work specifications for a set of work objects (eg, all work objects to be processed) in an integrated manner for a user selected prediction time period. The prediction time period for this integrated view may be specified independently from the processing time periods of the individual work objects. The prediction time may be chosen longer or shorter than the processing time period.

In embodiments, the predictor component includes a pre-trained machine learning component. In embodiments, the predictor component is configured in a neural network architecture, but other techniques such as support vector machines, decision tree are also envisaged in different embodiments.

In embodiments, the neural network architecture comprises at least one hidden layer. This is of particular benefit in radiation therapy applications, mainly, but not exclusively, envisaged herein. Using one or more, such as two or three, or yet even more, hidden layers may allow robust learning of underlying patterns in the patient characteristics and/or contextual data that are likely to lead to situations where specification changes become necessary.

In embodiments, the one or more processing devices comprises any one or combination of: a radiation therapy device, an imaging device, a computer system configured to run a therapy planning algorithm, a computer system configured to run an image segmentation algorithm.

In embodiments, the work object is a patient undergoing, or to undergo, radiation therapy.

In embodiments, the system is implemented in parts by at least one multi-core processing unit.

According to another aspect, there is provided a computer-implemented method for resource management, comprising the steps of:

receiving input data including one or more characteristics of at least one work object and/or including context data, the at least one work object to be processed by one or more processing devices, the said processing being specified in a respective work specification; and predicting, based on the input data, a change to the work specification; and providing output data that represent said predicted change.

According to another aspect, there is provided a computer program element, which, when being executed by at least one processing unit, is adapted to cause the processing unit to perform the method as per any one of the above described embodiments.

According to another aspect, there is provided a computer readable medium having stored thereon the program element.

In embodiments, the proposed system and method addresses changing workflows in RT. Protocol tasks are no longer fixed for the entire treatment procedure. Patient response is checked and monitored during treatment and based on this the physician may decide to change the task list during treatment. The task list for the treatment is therefore no longer statically defined. Even if some of this is factored in, there may be unforeseen plan changes.

Whether or not a treatment plan change may be necessary will depend on the patient and may vary throughout the patient population. The need for a plan change may depend of the type and anatomy of the tumor, personal characteristics of the patient and the occurrence and severity of side effect during treatment, and other factors or combinations thereof.

In RT it is important for patients that their treatment can be continued as smoothly as possible, without interruption or delay. This need is addressed by the proposed system. The system is configured to predict when in the future a plan change will be likely required so that the necessary resources to carry these changes into practice can be allocated before the decision to actually carry out the changes is taken by the healthcare professionals (referred to herein as "the user"). This need can be further addressed by having in embodiments a user functionality through which the time interval for the prediction can be specified by the user as desired. For instance, the predication may be requested for the next n-days, n being any number≥1, such as 10 or other.

In embodiments, the system can predict from the input data, such as personal information and diagnosis, how likely it is that the task list ("plan") for a patient will need to change, and what the impact on the resources of such a change will be. In embodiments, machine learning is used to learn probabilities from a previous patient population history.

The proposed system is configured to predict what resources are likely to be needed for optimal patient treatment. In embodiments, the system predicts how many tasks of each type are most likely to occur in the upcoming period due to changes. Tasks are only fixed again in an updated plan once the user has taken the actual decision on how to proceed. In embodiments, a workload evolution prediction is provided which may help scheduling and/or allocating equipment resources to RT that are shared between various departments, e.g. CT imaging that is shared between cardio and RT, etc.

BRIEF DESCRIPTION OF THE DRAWINGS

Exemplary embodiments of the invention will now be described with reference to the following drawings, wherein.

DETAILED DESCRIPTION OF EMBODIMENTS

Figure 1:
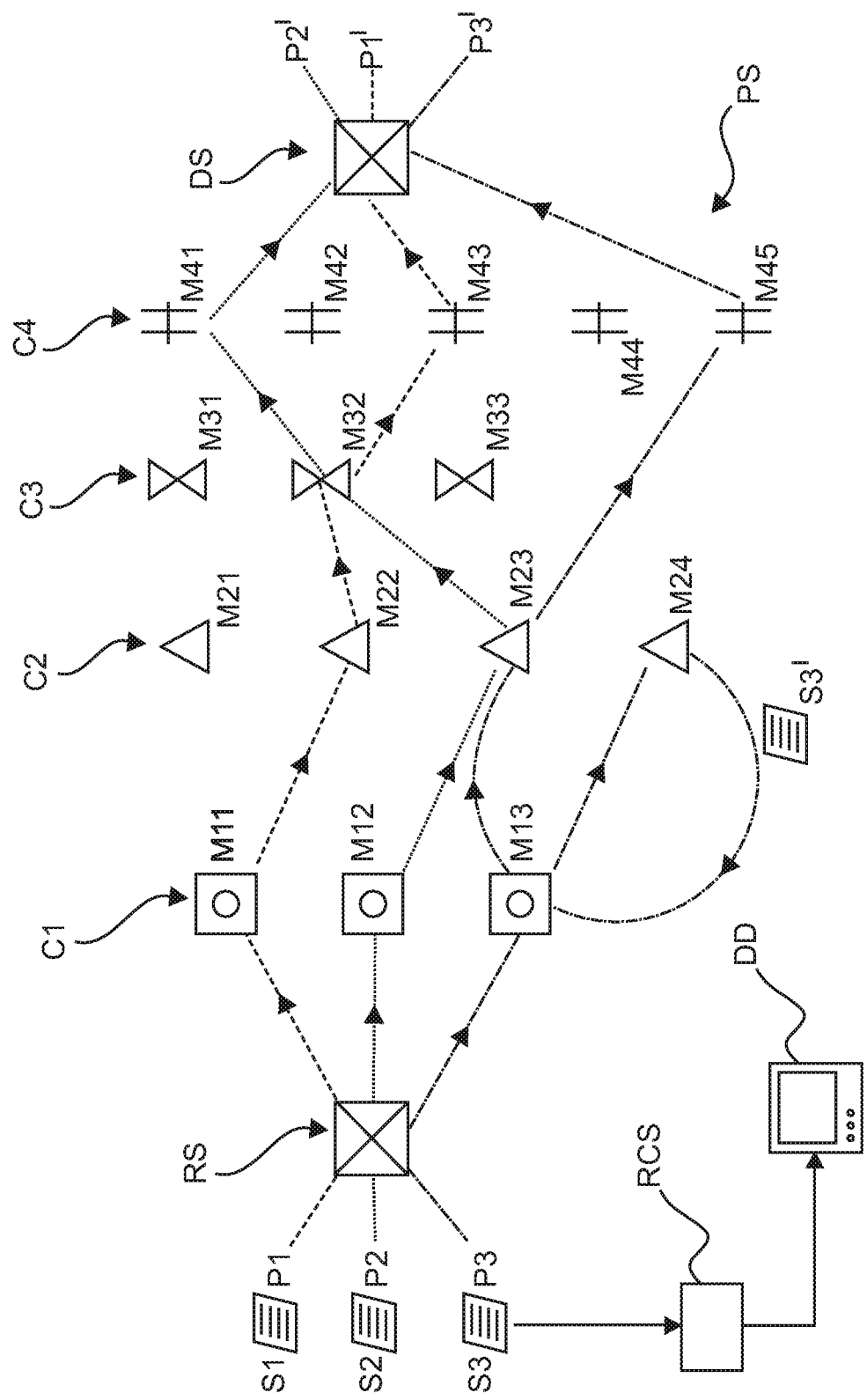
FIG. 1 shows a schematic block diagram of a processing facility.

With reference to FIG. 1, there is shown a schematic block diagram of a processing facility PS as envisaged herein in embodiments.

The processing facility PS includes a plurality of processing devices, such as machine equipment or other, schematically shown in the FIG. 1 as M11, M12, M21, M22, M23, M24, M31, M32, M33, M41, M42, M43, M44 and M45 (hereinafter "$M_{ij}$").

Each item of equipment $M_{ij}$ is configured to process one or more work objects P1 to P3 that are received at a receiving section RS.

The set-up of processing devices $M_{ij}$ to be used may be conceptually divided into categories C1-C4. Only 4 are shown but there may be less or more. The category determines which type of work a processing device i in the respective category j is capable of performing.

Each work object P1, P2, P3 is preferably associated with a specification S1, S2, S3 that specifies how the respective work object P1-P3 is to be processed by one or more of the processing devices $M_{ij}$.

As done in FIG. 1, the work specifications S1-S3 determine respective processing paths (shown in different line types, dotted, dashed, dashed-dotted) along which the respective work object proceeds through the processing facility PS. Although in FIG. 1 each category C1-C4 includes a plurality of respective processing devices in the respective category, this is exemplary and some or more of the categories may include only a single processing device.

Preferably the processing facility PS is configured to process a plurality of work objects at the same time. Each work objects P1-P3 is expected to proceed along its respective work path as per their associated specification S1-S3. Not all processing devices may be configured to process more than one work object at the same time. At least initially, the specifications may be configured at the receiving section by a scheduler SH (shown in FIG. 2) so that no conflict arises where two work objects compete for a given processing device at the same time.

At the conclusion of the processing the processed work objects, now indicated as P1', P2', P3' are then discharged (not necessarily at the same time) at discharge section DS.

The term "work object" as used herein is a generic term that may refer to animate or inanimate "objects". In one embodiment the processing facility PS is a radiation therapy department of a medical facility such as a hospital, or of a group of hospitals organized at regional or national level for instance.

However, it will be understood that the principles explained above and below are applicable to any type of processing not necessarily tied to radiation therapy to which main reference will be made in the following. In alternative embodiments, processing plants for processing chemicals or spare parts, car assembly, aircraft assembly, etc. Other processing tasks in any other type of industry are also envisaged herein. Accordingly, in embodiments the processing devices $M_{ij}$ may include for instance machine equipment, such as robotic equipment configured to performing different tasks (such as welding or other) in relation to the work objects.

Turning now in more detail to the radiation therapy embodiment as mainly envisaged herein, the work objects P1, P2, P3 will now be referred to as patients P1-P3.

The processing categories C1-C4 envisaged for radiation therapy purposes include one or more of the following: medical imaging equipment, such as transmission or emission imaging (such as PET, SPECT). Transmission imaging may include in particular a computed tomography (CT) scanner. MRI scanners are also envisaged herein. The categories C1-C4 for radiation therapy may further include image analysis tools to analyze the imagery as produced by the imaging equipment. Further categories may include radiation therapy planning systems and radiation treatment units such as a linac (linear accelerator system) or other.

A general work flow for a patient undergoing radiation therapy may be formulated in terms of the above mentioned work equipment as follows: initially a patient is imaged so that a medical professional can localize a lesion to be treated and obtain an idea about its extent. The imagery is then analyzed by image analysis tools. The image analysis tool may be implemented as a segmentation algorithm that runs on a computing system ("segmentor"), general or dedicated.

The segmentation algorithm reads in the imagery and then operates to delineate the lesion in the imagery. Through a wired or wireless connection, medical records of the patient may be accessed at any stage through a computerized database system such as HIS to obtain medical data of the given patient. Based on the segmented image and possibly on the medical data, a treatment planning system is operated to compute a respective treatment plan S1 for the given patient P1. The treatment plan includes, in particular, control parameters to control the LINAC during radiation delivery. The radiation is delivered in parts over a treatment period T in "fractions". In other words, the total radiation dose is delivered in one or more treatment sessions, requiring multiple revisits of the LINAC during T. "T" is usually in the order of 10-30 days. Other items of processing device $M_{ij}$ may also need to be revisited as described in the treatment plan to check how the treatment progresses, that is whether and what kind of effect the treatment plan has on the lesion. The revisits in during the treatment period may include reimaging of the lesion and possibly re-segmentation. The processing paths, or, in this context, "treatment paths" are hence in general circular rather than linear as shown in FIG. 1.

In particular, radiation therapy planning systems are provided as optimization algorithms that are run on a computer system, either general or dedicated. Because of the complexities involved in drawing up the LINAC control program, the computing system is preferably arranged as high performance computing system with a suitable chipset and/or micro-processors, such as multicore processor, GPUs or other. The treatment planning step includes in particular, the following which will be explained with exemplary reference IMRT (intensity modulated radiation therapy), with the understanding that this does not exclude other types of RT (radiation therapy) where computations may also be required. The control program computed is configured to call a multi-leaf (MLF) collimator equipment. The MLF collimator is operated by the linac to control the manner of exposure of the lesion. The lesion is exposed from different directions by rotating a treatment head around the lesion. The X-radiation beam, and hence the dose delivered, is controlled by the MLF collimator so as to conform in shape to the lesion. There is tradeoff to destroy as much of the lesioned tissue as possible but spare as much as possible the healthy tissue around the lesion.

A radiation therapy plan includes in particular a quantity known as a "fluence map". The fluence map $\varphi$ defines the intensity of the treatment beam across its cross section. More particularly, a treatment beam (also called an elementary beam), for a given radiation direction (as per the treatment head's position relative to the ROI) is comprised from single rays called "beamlets". Each elementary beam is determined by its angular position (or direction $\alpha$), its initial energy and its (2D) fluence map $\varphi_i$. The fluence map comprises elements called "bixels". The number of bixels in each fluence map is equal to the number of beamlets for the given elementary beam. Each bixel defines a "weight" (that is, a number) for a particular beamlet. This weight expresses the contribution of said beamlet to the dose delivered along said direction. In IMRT then, the total irradiated dose is composed by the superposition of several independent elementary beams, one static beam per each angular direction. Usually, between 5-14 (but this number is exemplary only) delivery directions are used in IMRT.

The radiation therapy planning system, in particular, computes an optimized fluence map of each lesion of each patient P1-P3. Based on the computed fluence map, a leaf sequencing tool computes the control program to control position and timing motions of the individual leaves of the MLF collimator. The computing of the fluence map is a computationally complex procedure that involves an optimization of a functional F that defines objectives. The optimization is constrained to account for the above-mentioned tradeoff. The computation is, in particular, based on the segmented 3D CT image that defines the lesion. The computation of the fluence map amounts to solving a positivity-constrained optimization problem with known methods. See for instance Pflugfelder et al, "*A comparison of three optimization algorithms for intensity modulated radiation therapy*", Z. Med. Phys. (2008) Vol. 18, No. 2, pp. 111-119.

In the cause of the treatment, the imager and the segmentor may need to be revisited a number of predefined times as per the treatment plan to produce updated segmented "control images", sometime called a respective "image of the day" although the frequency may not necessarily be daily. The updated imagery allows the healthcare processional to monitor how the lesion responds to radiation. There may then be the need to recompute the fluence map a number of times based on the updated imagery. In general, there is an expectation on how many image retakes may be required, and this expectation is factored into the initial treatment plan.

The above summarized steps for RT (radiation therapy) may need to be performed individually for each patient, and patient numbers at a given facility may easily run in the upper tens or hundreds. In particular, the radiation therapy planning systems and the LINAC are expensive items of equipment and there may be, at a given facility, only a single one of these available. To ensure each patient can be treated continuously, that is, as per their treatment plan without un-planned interruptions, resource conflicts should be avoided. To this end, a scheduler SH may be used to determine which patient is to be treated on which day (specified by date and preferably time slot) at which machine equipment $M_{ij}$ based on the treatment plan to produce a scheduled treatment plan. This scheduling information is then encoded in an initial treatment plan that may be created at the receiving section RS after patient check in at receiving section of the hospital facility and after consultation with a medical professional such as a radiologist or oncologist. Sometimes, the treatment plan has already been drawn up before or elsewhere. In this case, a computer system at the receiving section may be used to draw up the patient's record and to retrieve the respective treatment plan. The scheduler then includes the scheduling information to so formulate the respective initial scheduled treatment plans S1-S3. It is in particular the scheduled treatment plans that will be referred to herein as plans "S1-S3" or similar.

It has been observed by Applicant that the initial treatment plans S1-S3 do not necessarily stay constant for each patient throughout the treatment. Plan adaptations ("changes") may be required, even when, in embodiments, some image retakes, re-segmentations and/or some RT plan re-computations have been factored in. The plan changes may entail initially unforeseen iterations, or unforeseen iterations, at or revisits of certain ones of the processing devices. For instance, more re-planning at the treatment planning facility station may be required should the lesion change unexpectedly during treatment. Also, more control imagery at the CT or MRI imager may be required than originally planned. Accordingly, more visits to the segmentor may be required than planned, and so on.

Such a plan adaption S3' is schematically shown as the unplanned revisit for patient P3 of device $M_{13}$ resulting in an unforeseen cycle shown as the curved portion of the dashed-dotted path of patient P3. This may lead to conflict at device $M_{13}$, for instance in relation to patient P1.

These plan changes make meaningful scheduling difficult. Not all patients however, will need to have their plan adapted during treatment. It is only for a certain sub-set of patients where this is necessary. However, this may be enough to disturb the overall work flow in the facility PS.

Applicant has found that a proportion of patients whose treatment plan needs to be changed is different among different medical facilities. This may have to do with different characteristics of the patient population that are served by the facility PS in a certain area. Applicant has discovered that it would be beneficial to understand the functional relationship between the characteristics of a certain patient population at a site PS, and the likelihood for adaptations to the treatment plans to arise during the treatment period T.

This relationship may conceptualize as a mapping from the space of patient characteristics into a space of plan change occurrence. This mapping is likely to be a complex one and may not be easily captured by traditional tools such as statistical techniques. It is therefore proposed herein to provide a computerized resource management RCS system. It operates as work evolution predictor system to predict workload changes for the resources such as the devices $M_{ij}$ of processing facility PS. The resource management system RCS (also referred to herein as the workload evolution predictor system) includes a predictor component PC to perform the prediction of workload changes. The predictor component may include a machine learning sub-system or component MLC. In preferred embodiments (but not necessarily in all embodiments) the machine learning component MLC implements a machine learning algorithm which is configured to predict the expected workload for an RT department due to plan adaptation at a point in time in the future. The prediction is based on information drawn from the current patient population and/or contextual data. The resource workload evolution predictor system RCS computes, based on patient characteristic data and/or contextual data (such as season or other), an indicator that is configured to indicate whether plan changes can be expected for the currently checked-in patient population P1-P3.

The indication of the output data may be provided in a plurality of different forms which include probability densities, probability distributions, histograms or any other. Non-probabilistic indications are also envisaged. Furthermore, although machine learning algorithms are mainly envisaged herein, that is not to say that the mentioned statistical tools or other types of algorithms are to be excluded herein. Specifically, any other modelling, data processing, statistical or other, not necessarily ML based, are specifically envisaged herein, if the above-mentioned mapping can be suitably approximated.

Preferably the indication for the plan changes so computed may be visually rendered in graphical form on a display device DD such as a computer monitor. On the other hand, textual indications in addition or instead of graphical ones are not excluded herein.

The system RCS may be implemented as suitable software components on a computing unit PU, either general purpose or dedicated. Preferably the decided or general purpose computing system PU may include one or more processors. In particular, one or more multi-core processors such as GPU (graphics processor unit) or TPU (tensor processing unit) may be used. A single one or a plurality of computing units may be used, possibly arranged as server(s) communicatively coupled in a communication network such as in a Cloud architecture. In particular, the computing for the machine learning component may be so outsourced to one or more servers. As an alternative to a purely software based implementation, some or all of the components of the system RCS may be implemented as hardware components such as FPGAs or ASICS.

Figure 2:
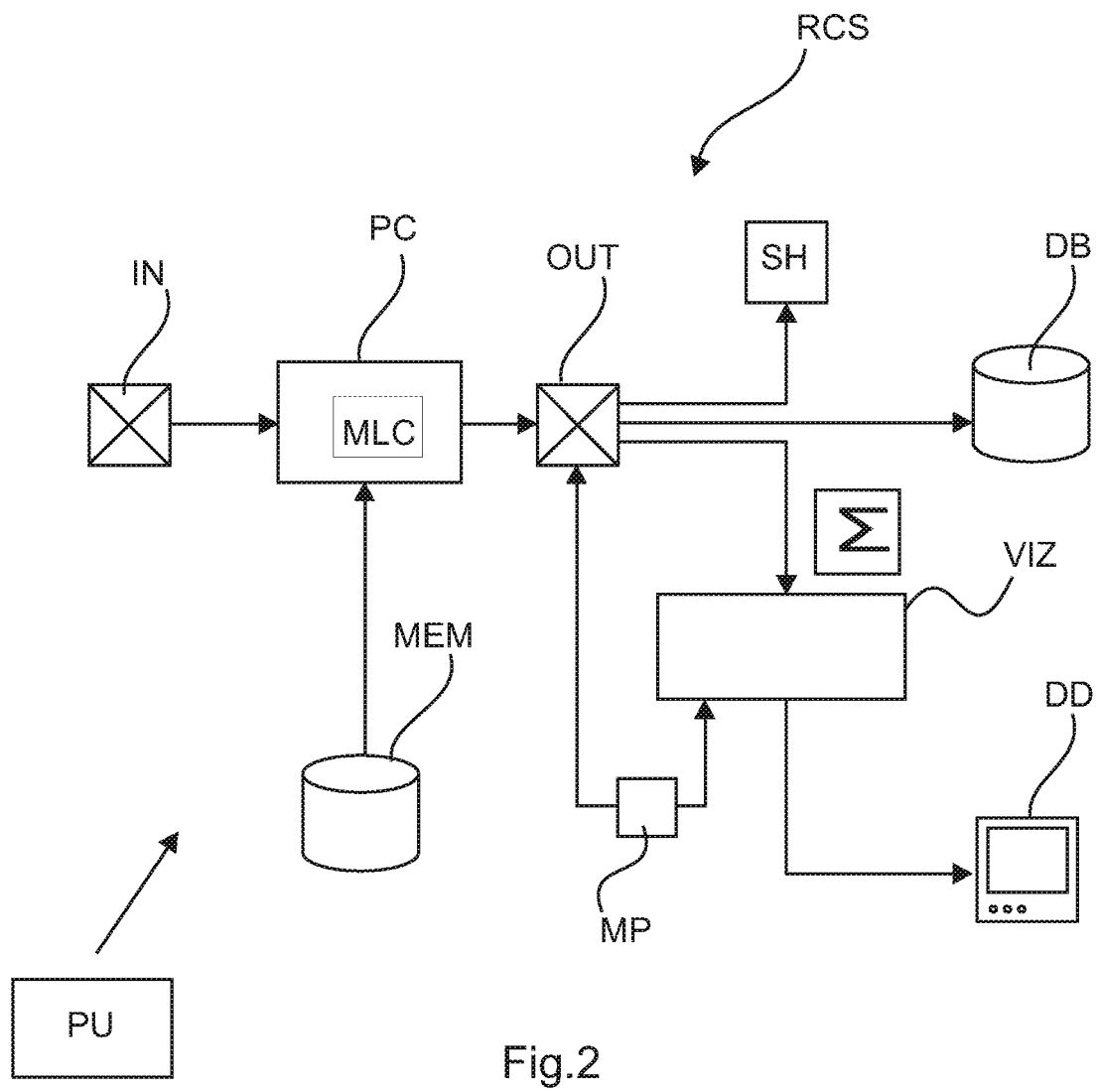
FIG. 2 shows a block diagram of a computerized resource management system.

Reference is now made to the block diagram of FIG. 2 where a schematic block diagram of system RCS is shown in more detail.

System RCS include an input port or interface IN through which input data is received. The input data includes patient characteristic data for the current population, optionally supplemented with contextual data such as data indicative of the current season (summer, winter, spring, autumn) and/or others. This input data is then processed in embodiments by a predictor component PC, such as a machine learning component MLC.

The machine learning component may be implemented in a neural network ("NN") architecture as will be explained in more detail below at FIG. 5 or it may be implemented by other ML techniques such as support vector machines, decision trees, regression algorithms or other.

The machine learning component MLC processes this input data and produces output data. Output data is suitable to indicate whether, and preferably when, during the treatment a plan adaption is likely to occur. The output data can be provided per patient or may be mapped by a mapper MP to an indication per equipment $M_{ij}$. Alternatively, the output data may be provided for sets (such as some or all) of patients and equipment $M_{ij}$ by accumulation over the sets, such as by summing, averaging, etc., by an accumulator circuit Σ (hereinafter "accumulator").

The projected treatment period T is usually around 10-30 days, but this is exemplary, and may be sub-divided into suitable time units such as days or hours.

The output data may be provided in the form of a discrete probability density over the treatment period. This form of output may be provided as a vector where each entry indicates a probability for a change of the treatment planned to occur at that date.

Richer output data is also envisaged as represented as a 2- or higher-dimensional matrix. A matrix entry does not only indicate whether a change is expected to occur and/or when, but also which item or at least which category of processing device $M_{ij}$ is involved in the change. As an alternative to this potentially high-dimensional output, a more simplified embodiment is also envisaged where the output is simply an indication by a binary unit that simply indicates whether a change is to be expected or not.

Preferably, the output by the machine learning component is in the form of indications per patient. In embodiments these indications may be accumulated by the accumulator Σ by summing over the respective entries in the output matrices or vectors so that the total number of changes for a given instant throughout the treatment period T may be provided.

The output data provided by the machine learning component MLC at output port OUT may be provided to the scheduler SH that may then use this data to re-schedule the originally drawn up treatment plans P1-P3. The output data may be stored in a memory DB.

The output data may be provided a display device DD, such as computer monitor by a display circuit (not shown) (herinafter "visualizer").

The output data may also or instead be mapped to per equipment and changes per item of equipment and expected workload.

Figure 3:
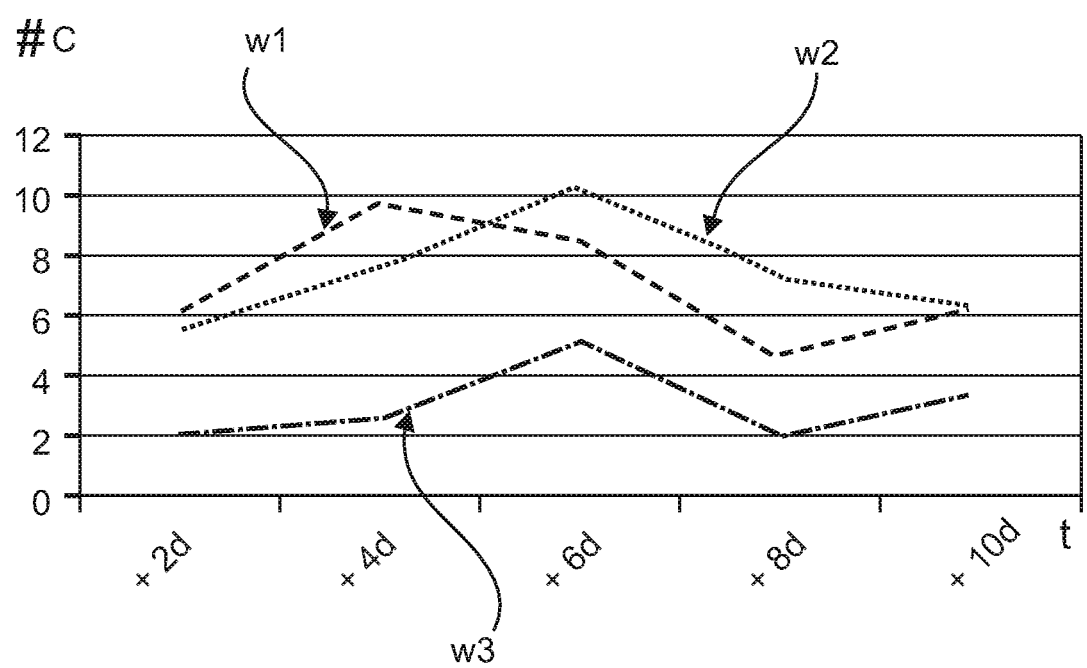
FIG. 3 shows a graphical indication produced by the module in FIG. 3.

With reference to FIG. 3 this shows an exemplary visualization w1,w2,w3 of the output data, in this case mapped to respective items of the processing devices M1, M2, M3. The indications in this embodiment are probability densities, represented as number of changes "C" graphed versus treatment days "d" which may extend over the whole treatment period or over any user specifiable interval from a reference point $T_{rf}$ up to the specified time interval extending into the future. Alternative, the vertical axis C may indicate workload, that is, the number of patients to be processed as a result of one more change. At this stage, the visualization indicates the workload quantity as a theoretically expected one, and not the actual re-planned workload. The actual re-planned workload may be computed by the scheduler SH and visualized in a similar diagram as in FIG. 3. Optionally, the currently planned works loads, as computable from all currently scheduled treatment plans, may in addition be displayed together with the visualization of the MLC output data. The data may be together displayed by the visualizer VIZ superimposed on the same diagram, preferably suitably visually differentiate by color-coding. Alternatively, the diagrams may be displayed in different panes on the same monitor or on different monitors. Yet alternatively, the user may be able to toggle between the output data as predicted and the currently scheduled plans S1-S3.

It can be seen for instance in the example diagram of FIG. 3 that for machine equipment w3 a relatively large number of changes can be expected at day 6. The expected number of changes is in the region of 5. It can also be seen for instance that machine equipment MT will see the largest number of changes at about day 6 in the region of 10 changes.

However, the visualizations as per FIG. 3 is merely one embodiment and other types of visualizations are not excluded herein, such as purely textual or other graphical renderings such as based on re-mappings of the output data.

The collection of all processing devices may be understood as parts of a complex super-system. The indication as per FIG. 3 or otherwise on workload evolutions when mapped onto the processing devices, and hence onto the super-system, may be understood as a dashboard of internal states of the super-system.

Before deployment, the machine learning component may need to be trained based on historical data held in the one or more memories MEM, such as in medical records of one or more hospital information systems HIS (hospital information system) or PACS (picture archive communication system). Specifically, the computerized predictor component is configured to correlate patient population characteristics (possibly augmented by context data) to plan adaptation incidence.

Preferably the predictor component may be arranged in a machine learning framework, operable in two phases or modes.

In the first part (the training phase or mode), the chosen framework is presented with patient characteristics data drawn from a patient populations and the corresponding number or rate of plan adaptation incidents.

Whilst providing individualized training data (i.e. treatment plans with known adaptation status on a per-plan basis) may require fewer training cases, it is not strictly required to know for whether plan adaptation was performed on a case-by-case basis—which simplifies the acquisition of training data. Historical data, e.g. obtainable from a data repository MEM such as an Oncology information system ("OIS"). OIS records all events of plan changes for a given patient, as well as all treatment incidences (fractions). Imaging related events can typically be retrieved from relevant timestamps in DICOM header files of the image data or from other information held in an image database such as in PACS. From these information items, the number or rate of plan adaptations can be calculated as the total amount of plan changes on a given day relative to the number of patients in treatment at that day. Probabilities are in general conditional on, e.g., disease type, length of treatment so far, and other factors. Rather than proceeding per day, other time element intervals may be chosen, such as per hour, per h hours (eg, h=12) fortnightly, weekly per month, etc. Because the probabilities relate to a whole set of patients, these may be called accumulated probabilities which may be averaged or otherwise further processed.

During this learning phase, a framework is generated (on which more further below at FIG. 5) that is capable to predict the rate of plan adaptation incidents for the corresponding patient population.

Once suitably trained, the MLC is ready for deployment and is now ready to receive the data for a currently treated number of patients to produce preferably graphical indications as for instance according to FIG. 3 or others.

More particularly, in the second phase, the deployment or application phase, the pre-trained network is provided with the patient population that is currently treated at a given facility PS. The data is then processed by the computerized framework. The framework returns the expected workload for plan adaptation in a defined time period in the future (e.g. the next two weeks). The proposed system hence allows more reliable scheduling for patients and equipment (and also workforce) accordingly to balance the workload, as exemplary shown in FIG. 3.

Figure 4:
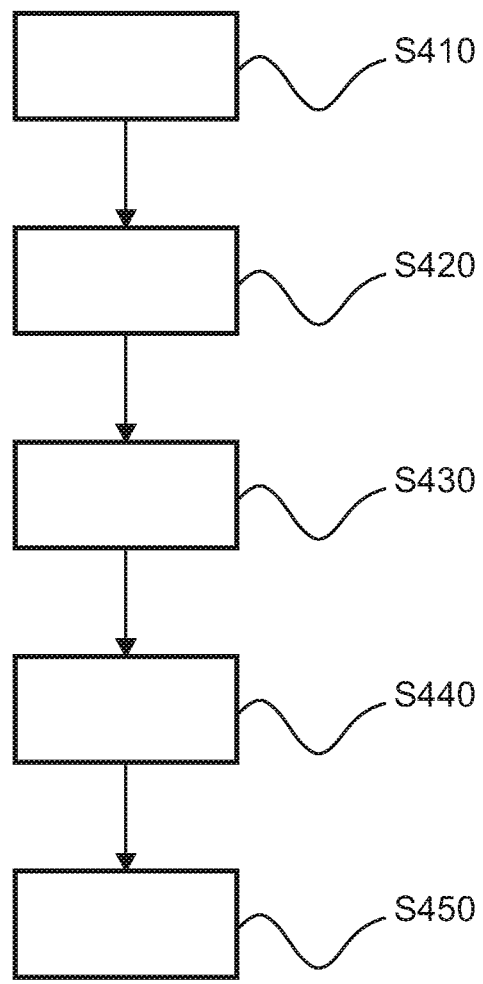
FIG. 4 shows a flow chart of a method for resource management.

Reference is now made to FIG. 4 that shows a schematic block diagram of a method for resource management that may underlie operation of the above described RCS. However, it will be understood that the following method steps may also be understood as a teaching in their own right and may not necessarily be tied to the architecture as per the RCS as described above in FIGS. 1-3.

At step S410 input data is received that includes patient characteristics for one or more patients of a population to be treated at a radiation therapy department PS.

The patient characteristics may include any one or more in any combination of the following: i) the initial RT plan itself, possibly along with derived sub-characteristics such as DVHs or distance between the target and certain risk organs, ii) bio-characteristics such as age, sex, BMI, iii) items of the medical record of the patient, iv) data items that represent a socio-economic situation of the patient. This set of patient characteristics is not exhaustive.

Optionally, the input data further includes contextual data that describe context or circumstances at the facility, for the patient or for the treatment.

The term "context data" in RT embodiments to data that represent state of affair that may have an influence of health, response to treatment of patient or data that relate to circumstances in effect at start or during the course of the processing.

Each patient is associated with a specification such as a treatment plan. The treatment plan specifies which devices or which category of devices are to be used at which date and, possibly, time slot. Optionally, the treatment plan may further specify treatment duration at some or each of the devices or device categories.

The treatment plan specifies on which days throughout a respective treatment period T, the respective patient is to be treated by which machine equipment $M_{ij}$. More generally, treatment plan is a scheduled treatment plan drawn up manually or by a computerized scheduler SH that assigns to each task in the treatment plan a device or device category to carry out the task, at which date/time slot and preferably for how long. The schedule thus transforms the treatment plan into a scheduled treatment plan.

At step S420 a change to the specification for one or more patients is predicted. The prediction quantifies where a change to the one treatment plans can be expected at one point in time during the projected treatment period T The prediction is computed based on the patient characteristics and/or contextual data. The prediction is suitably quantified in form of output data. Preferably, the prediction step is performed sequentially or in parallel for a single patient or more patients who currently has a scheduled treatment plan.

Preferably, the prediction step S420 is done for all patients with a (scheduled) treatment plan at a given PS medical facility or group of medical facilities (such as hospitals, cancer treatment centers, etc). The treatment periods T for the patients may not necessarily commence on the same day.

Preferably, the change predicted at step S420 or adaptation to a current treatment plan relates to a change that may affect treatment plan processing of at least one other patient currently registered at the same processing facility or group of facilities. Specifically, the predicted change may include any one or more of: i) a change from one device to another device of a different category for a given task in the current plan, or ii) a change of treatment duration for a given task at a given device or device category, or iii) adding a new task at the same or different device or category, or iv) omitting a slated task.

Preferably the step S420 is not a one-off operation but may be periodically repeated to account for new patients. For instance, the step S420 may be triggered each time a new patient has their scheduled treatment plan logged onto the scheduler.

At step S430 the output data is provided for storage, visualization or other type of processing. The outputting step S430 may include reformatting, accumulating or remapping as will be explained in more detail below.

The output data may include an indication for the predicted change or changes per patient, per group of patients, per device or group of devices, or per device category.

The output data may be indicated as continuous or discrete curves over a, preferably user configurable, time interval. The time interval may extend for the whole treatment period or may be restricted to only a sub-interval thereof. The time interval may also extend beyond the treatment period so as to account for the circumstance that not all patients may commence their treatment on the same day and/or there may be treatments of different lengths for different patients.

In an optional step S440, the output data for the devices or categories of devices is accumulated by summation over the treatment plan changes for some or all patients to derive at the total of expected workload per device or category of device.

In embodiments the curves indicate the individual changes per patient in absolute sums or normalized sums. In embodiments, the curves include any one or more of a histogram, probability density or distribution or other numerical format.

At step S450 the output data or accumulated output data is visualized on a display device. In embodiments, the curves are displayed in a graphics display, including, but not limited to, in the manner as shown in FIG. 3.

Preferably in an embodiment where step S420 is implemented by a machine learning algorithm, the output data may be organized in scalar, vector, matrix or tensor (being a matrix of dimension larger than 2) form.

In a simple embodiment is binary (x="1" or "0") to indicate whether plan adaptation is expected per patient. This may be encoded in a scalar, for example, by convention x="1" for the prediction that a change is expected for given patient or no change is to be expected, x="0". This and following encodings are exemplary, and others are also envisaged. These scalar indications per patient may be consolidated into a binary vector, with length that of the number of current patients. The above may be mapped onto corresponding scalars or vector not per patient but per processing device or device category.

Preferably, the output data may be augmented for richer information such as in vector form, for example for each patient, (d, ID, tΔ), with d being a day during treatment period T where the change is predicted to occur, and the two other organizational dimensions indicating the nature of the expected change. For instance, tΔ may indicate the change of treatment duration, and ID is a suitable encoding for the new device or new category of device predicted to change over time. In each of the three dimensions, a "0" is indicative of no change. These encodings and order of the vector components are exemplary, and alternatives thereto are also envisaged herein.

For yet a more augmented output data format, for each patient one may obtain as output an associated adaptation matrix A that encodes in more detail the nature or the change incurred: $A=a_{ij}$="1" or "0" indicating, by convention, a change from resource i to resource j. "1" indicating there is a change from resource i to j and "0" indicating there is no such change. Summing for j over all i and over all patients is then the new load to be expected at i given the plan changes. The adaption matrix may be reformulated in terms of device category rather than in terms of individual devices. The adaption matrix may be augmented by a further dimension representing each day during the treatment period so that the predicted changes may be represented per time intervals, such as per days, hours etc. of the treatment period. The adaptation matrix may be further augmented to include further dimensions for the changes of treatment duration at the respective device or category.

Representation in terms of probability density is also envisaged in embodiments. In embodiments, the output for each patient includes a probability vector that represents the probability for change to occur for a given patient's treatment plan. Each entry in the vector corresponds to a probability for a change and each position in the vector indicates the respective day, hour or other time unit during the treatment time T. in embodiments, probability for a plan change event is given as the number of plan changes over the number of patients currently in treatment. The probability is conditional on the patient characteristics.

Figure 5:
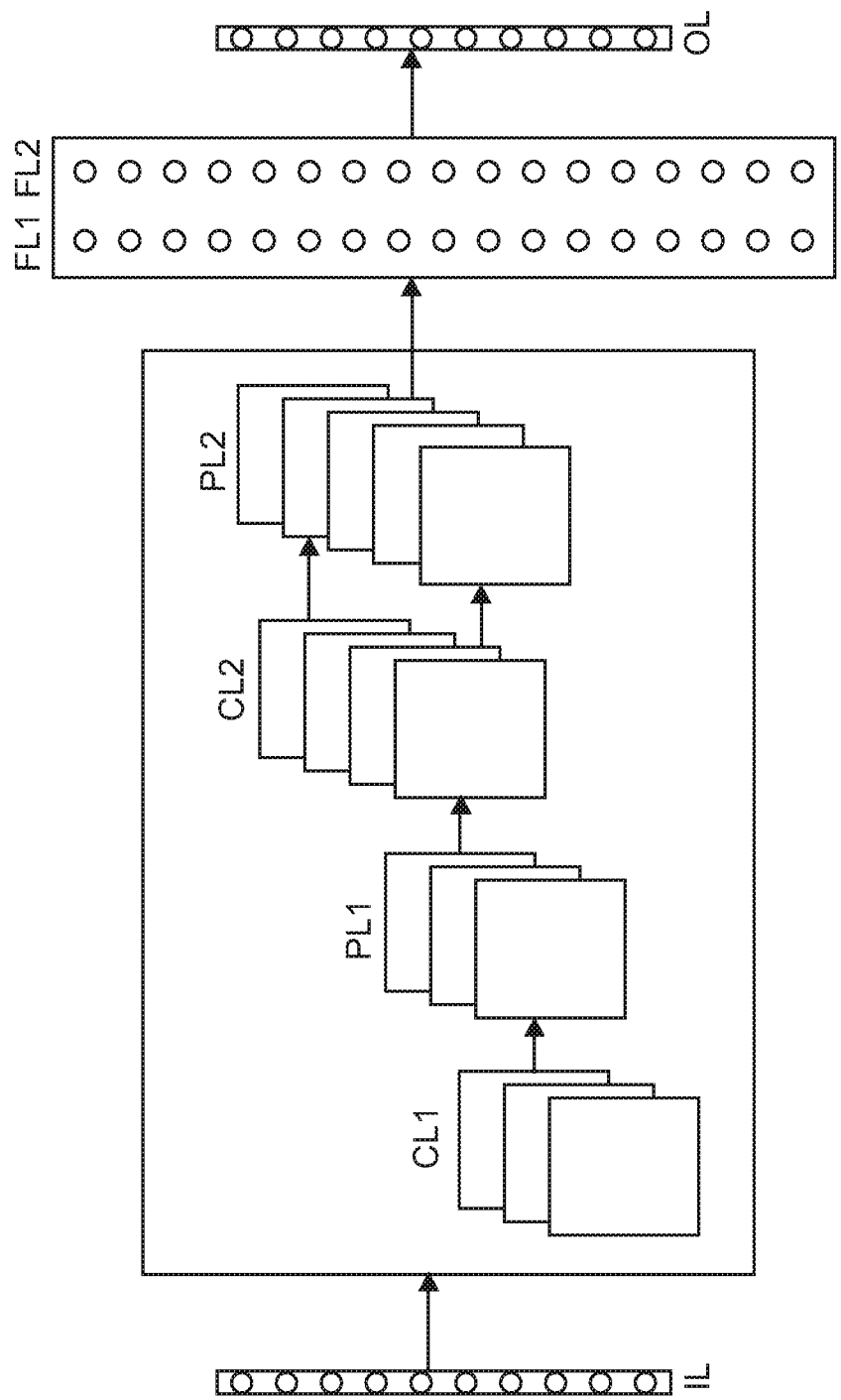
FIG. 5 shows neural network architecture implemented in embodiments of the module of FIG. 2.

Reference is now made to FIG. 5 and provides more details on the prediction step S420 which, as indicated above, may be implemented as a machine learning component, in particular an NN. In particular, and in embodiments, a convolutional neural-network CNN may be used as schematically shown in FIG. 5, however this is not at the exclusion of alternative embodiments such as support vector machines, linear regression algorithms, decision trees, or otherwise, all equally envisaged herein.

A fully configured NN as obtained after training (to be described more fully below) may be thought as a function representation of an approximation of the above mentioned mapping between the two spaces, namely the space of patient characteristic, possibly augmented by context data, and the space of plan change representations. A suitable trained machine learning component "encodes" this mapping. The machine learning component may be realized as neural-network ("NN"), in particular a convolutional neuro-network ("CNN"). With continued reference to FIG. 5, this shows in more detail a CNN architecture as envisaged herein in embodiments.

The CNN is operable in two modes: "training mode/phase" and "deployment mode/phase". In training mode, an initial model of the CNN is trained based on a set of training data to produce a trained CNN model. In deployment mode, the pre-trained CNN model is fed with non-training, new data, to operate during normal use of the SSI. The training mode may be a one-off operation or this is continued in repeated training phases to enhance performance. All that has been said so far in relation to the two modes is applicable to any kind of machine learning algorithms and is not restricted to CNNs or, for that matter, NNs.

The CNN comprises a set of interconnected nodes organized in layers. The CNN includes an output layer OL and an input layer IL. The CNN has preferably a deep learning architecture, that is, in between the OL and IL there is at least one, preferably two or more, hidden layers. Hidden layers may include one or more convolutional layers CL1, CL2 ("CL") and/or one or more pooling layers PL1, PL2 ("PL") and/or one or more fully connected layer FL1, FL2 ("FL"). CLs are not fully connected and/or connections from CL to a next layer may vary but are in generally fixed in FLs.

Nodes are associated with numbers, called "weights", that represent how the node responds to input from earlier nodes in a preceding layer.

The set of all weights defines a configuration of the CNN. In the learning phase, an initial configuration is adjusted based on the training data using a learning algorithm such as forward-backward ("FB")-propagation or other optimization schemes.

The training mode is preferably supervised, that is, is based on annotated training data. Annotated training data includes pairs or training data items. For each pair, one item is the training input data and the other item is target training data known a priori to be correctly associated with its training input data item. This association defines the annotation and is preferably provided by a human expert. In training mode preferably multiple such pairs are applied to the input layer to propagate through the CNN until an output emerges at OL. Initially, the output is in general different from the target. During the optimization, the initial configuration is readjusted so as to achieve a good match between input training data and their respective target for all pairs.

More specifically, the input training data items are applied to the input layer (IL) and passed through a cascaded group(s) of convolutional layers CL1, CL2 and possibly one or more pooling layers PL1, PL2, and are finally passed to one or more fully connected layers. The convolutional module is responsible for feature based learning (e.g. identifying features in the patient characteristics and context data, etc.), while the fully connected layers are responsible for more abstract learning, for instance, the impact of the features on the treatment. The impact on treatment plan is indicated by nodes in the output layer OL. In other words, the output layer OL includes the output data that represents the predicted changes (if any) from which the expected workload is either derivable or directly indicated in the nodes of the output layer OL.

The exact grouping and order of the layers as per FIG. 5 is but one exemplary embodiment, and other groupings and order of layers are also envisaged in different embodiments. Also, the number of layers of each type (that is, any one of CL, FL, PL) may differ from the arrangement shown in FIG. 5. The depth of the CNN may also differ from depth=6 as shown in FIG. 5. All that has been said above is of equal application to other NNs envisaged herein, such as fully connected classical perceptron type NN, deep or not, and recurrent NNs, or others. In variance to the above, unsupervised learning or reinforced leaning schemes may also be envisaged in different embodiments.

The annotated training data, for the MLC as envisaged herein may need to be reformatted into structured form. The annotated training data may be arranged as vectors or matrices or tensor (arrays of dimension higher than 2). This reformatting may be done by a data pre-processor module (not shown), such as scripting program or filter that runs through patient records of the HIS of the current facility to pull up a set of patient characteristics.

Preferably the training data relates to same population that is to be targeted in the deployment to better capture any peculiarities there may be for more accurate predictions when later serving that population in RT or other scheduling and device intensive care. In more detail, the training data for the CNN or other NN may comprises, for each patient p, a pair of patient data D(p) and associated incident data $IC_j$, each representable as vectors or matrices or tensors. Each such pair may be formalized as:

$$D(p)=(x_i, x_2, \ldots x_N) \rightarrow IC=(t_1, \ldots, t_j, \ldots, t_T), t_j=1,0 \qquad (1)$$

Each $x_i$ represents a patient characteristic datum or context, suitably encoded. In the incident data, a binary vector may be used in embodiments, each entry $t_j$ indicating whether a change at time increment j did, or did not occur, encoded by "1" or "0", respectively or according to other encoding scheme.

As mentioned above, the incident data may be augmented by association, for each patient p, an adaptation matrix that encodes the nature or the changes incurred in the past: again, $A_{ij}=a_{ij}=1,0$ indicating a change from resource i to resource j.

In deployment, the output data may be obtained by summing for j over all i is then the new, expected load to be expected at i given the plan changes.

In deployment, the output data for a one, more than one or all current patients may be grabbed by a scripting tool or other, and an accumulated sum may be formed $S=\Sigma_p IC_p$ over all or some of p. S may be normalized S/N to obtain a probability density for the number of changes to occur at each time element throughout T.

The training data sets are applied to the an initially configured CNN and is then processed according to a learning algorithm such as the FB-propagation algorithm as mentioned before. At the end of the training phase, the so pre-trained CNN may then be used in deployment phase to operate for resource management, in particular workload evolution predication as described above in FIGS. 1-4. The data provided at the output layer OL is not necessarily be visualized for the user, although this may still be done in embodiments. In other embodiments or in addition, the data as grabbed from the output layer and may be passed through further processing stages such as summation by the accumulator Σ or may be remapped by mapper MP and the so processed data is then provided as output data for visualization the display device DD or for yet further processing.

As mentioned earlier, s training data per each individual patient ("case-by-case") may not necessarily be required in all embodiments but instead data may be consolidated in "bulk". Specifically, the incident data IC may be represented as approximated probability densities. The approximation is by ratios per time intervals (eg, hour, day, etc) or other suitable division of the treatment period T. Each ratio is an approximation of the probabilities masses for the given time intervals. The incidents of all changes can be filtered out of the oncology information systems and or PACS data to from per time element ratios. The ratios may be formed in embodiments by dividing all so found changes by the total number of patients treated that day, hour, week, etc. The incident data IC (the right hand side of expression (1)) may hence be presented as $(f_1, f_2, \ldots f_N)$, each f a ratio as described, for some or each time point (eg, day, hour, or whatever the time element) $1 \leq i \leq N$ within the treatment period T. In this learning data consolidation embodiment, the left hand side of annotation (1) is then formed by all patient data characteristics (possibly augmented by contextual data) where a change occurred within the considered, respective time element intervals i.

More specifically, in deployment, patient characteristic data for patients to be treated are prepared or structured as described. The patient characteristic data is then applied to the input layer IL of the pre-trained neural network NN or CNN. The data is then propagated through the NN to obtain the output data that is indicative to plan changes from which in particular workload evolution may be derived for each device or device category.

The MLC helps to achieve accurate workload evolution predictions. In particular, when multi-core processors such as GPU or TPU or similar are used to implement the above, good responsiveness and high throughput can be secured, in the order of minutes, such as, for example, 3-5 mins.

In deployment, the output matrix at output layer OL may be visualized individually for each patient or may be individualized per device or device category.

If it is visualized per device or device category, the contributions from each change caused by each treatment plan change may be summed to provide accumulated probability for a total number of changes to be expected at a given day for the device or device category.

The indication for the changes may not necessarily be rendered for display for the entire treatment period T. A user may specify a sub-period for which the indication is required. For instance, even though the treatment period is usually 30 days, it may be desired to visualize not the whole 30 days but only a sub-section such as the first 10 days or similar or the period after the fifth up to the twentieth day or other desired time intervals of interest.

The components of system RCS may be implemented as software modules or routines in a single software suit and run on a general purpose computing unit PU such as a workstation. Alternatively, the components of the image processing system RCS may be arranged in a distributed architecture and connected in a suitable communication network.

Alternatively, some or all components may be arranged in hardware such as a suitably programmed FPGA (field-programmable-gate-array) or as hardwired IC chip.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A resource management system, comprising:
    an input port for receiving input data including one or more characteristics of at least one work object and comprising context data, the at least one work object to be processed by one or more processing devices ($M_{ij}$), the processing being specified in a respective work specification;
    a convolutional neural network (CNN) model created by training input data to predict, based on the input data, a change to the respective work specification;
    determine when a plan adaption is required based on a work specification; and
    an output port adapted to provide output data that represents the change to the respective work specification, wherein the output data indicate when, during a treatment, the plan adaption will occur.

2. The resource management system of claim 1, wherein the training of the CNN model further comprises training an initial model based on a set of training data to produce the CNN model.

3. The resource management system of claim 1, wherein in a deployment mode, the CNN model is provided new data to operate during use of the resource management system.

4. The resource management system of claim 1, wherein the created CNN model further is repeatedly trained.

5. The resource management system of claim 4, wherein the repeated training comprises repeatedly training the CNN model with new input data.

6. The resource management system of claim 4, wherein the respective work specification specifies a period of time for the processing.

7. The resource management system of claim 6, wherein the output data comprise a probability density or distribution over the period of time, the period of time comprising at least one time interval, the probability density, or distribution indicative of a probability of the predicted change to occur within a given one of the at least one time intervals.

8. The resource management system of claim 4, wherein the output data comprise a probability density or distribution over a period of time, which comprises at least one time interval, the probability density or distribution indicative of a probability of the predicted change to occur within a given one of the at least one time intervals.

9. The resource management system of claim 4, wherein the output data comprise an indication of an expected workload, due to the predicted change, for at least one of the one or more processing devices ($M_{ij}$) or for at least one category of devices.

10. The resource management system of claim 4, creating of the CNN model further comprise providing a pre-trained machine learning component.

11. The resource management system of claim 4, wherein the one or more processing devices comprises any one or a combination of: i) a radiation therapy device, ii) an imaging device, iii) a computer system configured to run a therapy planning algorithm, iv) a computer system configured to run an image segmentation algorithm.

12. The resource management system of claim 1, wherein there is plurality of work objects, and the resource management system further comprises an accumulator configured to accumulate the output data for the plurality of work objects.

13. The resource management system of claim 1, wherein the output data includes an indication of an expected workload, due to the predicted change, for at least one of the one or more processing devices or for at least one category of devices.

14. The resource management system of claim 13, comprising a display configured to effect a visualization of the output data or of the accumulated output data on at least one display device.

15. A method of managing a resource adapted to be implement by a processor, wherein a tangible, non-transitory computer-readable medium stores instructions, which when executed by the processor, causes the processor to:
    receive input data including one or more characteristics of at least one work object and comprising context data, the at least one work object to be processed by one or more processing devices ($M_{ij}$), the said processing being specified in a respective work specification;
    create a convolutional neural network (CNN) model by training input data to predict, based on the input data, a change to the respective work specification;
    determine when a plan adaptation is required based on a work specification; and
    provide output data that represents the change to the respective work specification, wherein the output data indicate when, during a treatment, the plan adaption will occur.

16. The method of claim 15, wherein the training of the CNN model further comprises training an initial model based on a set of training data to produce the CNN model.

17. The method of claim 15, wherein the instructions, when executed by the processor further cause the processor to deploy the CNN model by providing new data to operate during the method.

18. The method of claim 15, wherein the CNN network is created by repeating the training.

19. The method of claim 18, where the repeating the training comprises repeating the training with new input data.

20. The method of claim 15, wherein the output data comprise a probability density or distribution over a period of time, the period of time comprising at least one time interval, the probability density, or distribution indicative of a probability of the predicted change to occur within a given one of the at least one time intervals.

21. The resource management system of claim 1, wherein the output data further indicate at least which category of the one or more processing devices ($M_{ij}$) is involved in the change.

22. The method of claim 15, wherein the output data further indicate at least which category of the one or more processing devices ($M_{ij}$) is involved in the change.

* * * * *